(12) United States Patent
Ojamo et al.

(10) Patent No.: US 6,602,691 B1
(45) Date of Patent: Aug. 5, 2003

(54) PROCESS FOR THE PRODUCTION OF MANNITOL BY IMMOBILIZED MICRO-ORGANISMS

(75) Inventors: Heikki Ojamo, Lohja (FI); Hannu Koivikko, Kantvik (FI); Heikki Heikkilä, Espoo (FI)

(73) Assignee: Xyrofin Oy, Kotka (FI)

( * ) Notice: Subject to any disclaimer, the term of this patent is extended or adjusted under 35 U.S.C. 154(b) by 0 days.

(21) Appl. No.: 09/743,342

(22) PCT Filed: Jun. 29, 1999

(86) PCT No.: PCT/FI99/00573

§ 371 (c)(1),
(2), (4) Date: Jan. 9, 2001

(87) PCT Pub. No.: WO00/04181

PCT Pub. Date: Jan. 27, 2000

(30) Foreign Application Priority Data

Jul. 15, 1998 (FI) .................................................. 981615

(51) Int. Cl.[7] .................................................. C12P 7/18
(52) U.S. Cl. ........................ 435/158; 435/105; 435/176; 435/177; 435/178; 435/179; 435/180
(58) Field of Search ................................ 435/158, 105, 435/176, 177, 178, 179, 180

(56) References Cited

FOREIGN PATENT DOCUMENTS

| DE | 37 15857 A1 | 12/1988 |
|---|---|---|
| DE | 44 10 028 A1 | 11/1995 |
| EP | 0 683 152 A1 | 11/1995 |
| WO | WO 97/04120 | 2/1997 |

OTHER PUBLICATIONS

Stanbury et al, Principles of Fermentation Technology, Pergamon Press, New York, pp. 74–90 (Chapt. 4), 1984.*
Stanbury et al, Principles of Fermentation Technology, Pergamon Press, New York, pp. 145–168 (Chapter 8), 1984.*
Soetaert, W., *Biologish Jaarboek* 56: 24(1988).
Soetaert, W. et al., "A wide range of carbohydrate modifications by a single micro-organism: leuconostoc mesenteroides", *Progress in* Biotechnology, 10: 351–358 (1995).
Soetaert, W. et al., "Production of D–Mannitol and D–Lactic Acid from Starch Hydrolysates by Fermentation with Leuconostoc Mesenteroides", *CR. Acad. Agric. Fr.*, 80: 119–126 (1194).
"Lactic Acid Bacteria", *NATO ASI Series*, H98: 213–218 (1996).
Soetaert, W. et al., "Production of Mannitol With Leuconostoc mesenteroides" *Med. Fac. Landbouw. Rijksuniv.* Gent, 55/4: 1549–1553 (1990).
Soetaert, W. et al., "Production of D–mannitol and D–lactic acid by fermentation with Leuconostoc mesenteroides", *Argo–Food Industry Hi*–Tech, pp. 41–45 (Jan./Feb. 1995).
Yun et al., "Microbial Transformation of Fructose to Mannitol by Lactobacillus SP. KY–107" *Biotechnology Letters*, 18(1):35–40 (1996).
Onishi H. et al., "Microbial Production of D–Mannitol and D–Fructose from Glycerol", *Biotechnology and Bioengineering*, 12: 913–920 (1970).
Hendrickson et al., "Short Communication: Production of Mannitol by Penicillium Strains" *J. Chem. Tech. Biotechnol.*, 43: 223–228 (1988).
Chemicals Abstracts. Abstract 116: 172322, NATO ASI Series, Ser. A 207 (Bioorg. Chem. Healthcare Technol.) 245–250 (1991).
Soetaert W. et al., "Production of Mannitol by *Leuconostoc Mesenteroides*, Immobilized on Reticulated Polyurethane Foam", *Bioorganic Chemistry in Healtcare and Technology*, pp. 249–250 (1991).
Japanese Laid–Open No. JP60002191 Abstract (1985).
Japanses Laid–Open No. JP62239995 Abstract (1986).

* cited by examiner

*Primary Examiner*—Francisco Prats
(74) *Attorney, Agent, or Firm*—Scully, Scott, Murphy & Presser; Frank S. DiGiglio

(57) ABSTRACT

The invention relates to the production of mannitol by bioconversion with the aid of immobilized micro-organisms as well as to the use of the mannitol and by-products formed in the conversion process. In said process a solution containing a substrate convertible into mannitol is fed into contact with solid carrier particles containing viable mannitol-forming microorganism cells immobilized in and/or on said particles. The solution is reconditioned between successive conversion steps in order to provide conversion of a major portion of said substrate into mannitol.

48 Claims, No Drawings

PROCESS FOR THE PRODUCTION OF MANNITOL BY IMMOBILIZED MICRO-ORGANISMS

The present invention relates to the production of mannitol by bioconversion with the aid of immobilized micro-organisms, especially to the bioconversion of a mannitol producing substrate by viable immobilized mannitol-forming micro-organisms. The invention also relates to the use of the mannitol and by-products formed in the conversion process.

Mannitol is a six-carbon sugar alcohol having wide use in several industrial areas. Examples of food use are as a sweetener, an anti-caking and a free-flowing agent. Pharmaceutical applications are as an excipient and a diluent for solids and liquids, as an osmotic diuretic and as a protective agent in surgery. Mannitol is also used for making resins and plasticizers.

Low levels of mannitol are found in several fruits and vegetables. Some algae and mushrooms contain significant concentrations of mannitol. Mannitol has been recovered from manna and seaweeds. Presently mannitol is industrially produced by catalytic hydrogenation of fructose or glucose/fructose mixtures such as invert sugar. Raney-nickel is used as the catalyst. The disadvantage of this method is that only about half of the fructose is converted to mannitol. The other half goes to sorbitol as does all of the glucose. Mannitol is far less soluble in water than sorbitol and thus crystallization is used for the separation of these two compounds. As Raney-nickel is used as the catalyst, the raw material being hydrogenated must be quite pure to avoid poisoning of the catalyst.

Mannitol may be produced also from mannose and glucose by hydrogenation. Several micro-organisms are known to produce mannitol. Among bacteria a heterofermentative bacterium *Leuconostoc mesenteroides* seems to be the most efficient of these. Soetaert W., Med. Fac. Landbouw. Rijksuniv. Gent, (1990) 55/4:1549–52, has described this fermentative method with free cells providing a 80–90% yield of mannitol from fructose. Later Soetaert W. et al., Agro-Food Industry Hi-Tech, January/Febrary 1995:41–45, showed up to 94% yield with free cells in a fed-batch process with a mutant strain. This fed-batch fermentation resulted in an average volumetric productivity of 3.5 g/lh in a broth containing significant concentrations of nutrients to enable cell growth. Cell growth is a prerequisite for the production in such a system.

Soetaert et al., Bioorganic Chemistry in Healthcare and Technology, Eds. Pandit U. K. and Alderweireldt F. C., Plenum Press, New York, 1991, also tried to apply a continuous bioreactor with the cells immobilized on polyurethane, but the result was poor, achieving only about 50% yield of mannitol from fructose. In the above mentioned 1995 article Soetaert et al. explained this to be caused by the low affinity of the fructose to mannitol converting enzyme—mannitol dehydrogenase. According to Soetaert the low yield is a consequence of the use of an immobilized bioreactor.

EP 0 683 152, Araya et al. (1991), discloses a similar free cell method, but with a *Lactobacillus* sp. B0001 strain. This gives 60% yield of mannitol from fructose. They also claim separation of acetic acid and lactic acid from the broth.

In JP 62239995, Hideyuki et al. (1987), teaches a process wherein free cells of eg. *Lactobacillus brevis* IFO 3960 and *L. meselteroides* IFO 3426 are used for mannitol production.

Yun et al. Biotechnol. Lett. (1996), 18:1145–1150, give some data about a fermentative mannitol production with free cells of another lactic acid bacterium *Lactobacillus* sp. KY-107. No glucose addition is needed and the mannitol yield from fructose is 71%. Formation of other extracellular products are not shown. The average volumetric productivity can be calculated from the results to be about 0.9 g/lh.

Onishi et al., Biotechnol. Bioeng., (1970), 12:913–920, discloses a process providing a 50% yield of mannitol from glycerol with free cells of a *Torulopsis versatilis* strain.

Several filamentous fungi (molds) produce mannitol from glucose as well. According to Hendriksen et al., J. Chem. Tech. Biotechnol., (1988), 43: 223–228 the best of these is *Aspergillus candidus* giving a 50% yield of mannitol from glucose. Production with yeast and filamentous fungi gives lower volumetric productivities than with bacteria. All the reports work with free cells.

The prior art biotechnical processes for the conversion of sugars to mannitol have not proven entirely satisfactory and therefore the industrial production is still primarily based on hydrogenation. Bioconversions using free mannitol-forming microorganisms are not entirely suitable for large scale production and systems with immobilized systems have so far not provided an adequate conversion yield. The volumetric productivity of the prior art systems is low leading to uneconomical operations.

Thus, there remains a need for improving the bioconversion of fructose and other substrates into mannitol in order to provide an industrially acceptable process.

An object of the present invention is thus to overcome disadvantages of the prior art techniques for converting substrates into mannitol and to provide a technically feasible biotechnical process for the production of mannitol.

An object of the present invention is also to provide a process for converting suitable substrates into mannitol by viable micro-organisms immobilized on a solid carrier.

A further object of the invention is to provide a continuous process for converting substrates into mannitol in a packed column, in which the solution is reconditioned during the conversion for increasing the yield.

Another object of the invention is to provide a process wherein a solution containing a substrate convertible into mannitol is sequentially reconditioned to provide optimum conditions for the conversion by immobilized microorganisms.

An object of the invention is also to provide a process for producing mannitol in a packed column with a low resistance to flow and a low pressure drop at flow of a substrate solution through said column.

An object of the invention is also to provide a process which utilizes a packed column having an acceptable flow rate through the column.

An object of the invention is also to produce mannitol from fructose-containing solutions which inherently contain a co-substrate such as glucose for the conversion.

An object of the invention is further to provide a biotechnical process for producing mannitol at a relatively high volumetric productivity.

Surprisingly, and contrary to prior beliefs it has been found that mannitol may be advantageously produced by micro-organisms which are immobilized in and/or on a carrier.

The present invention is defined in the appended claims, the contents of which are enclosed herein by reference.

Accordingly, the invention relates to a process for the production of mannitol by bioconversion with the aid of immobilized micro-organisms. Said process comprises the steps of feeding a solution containing a substrate which is convertible into mannitol into contact with solid carrier particles containing viable mannitol-forming microorganism cells immobilized in and/or on said particles, under conditions suitable for converting said substrate into mannitol, reconditioning said solution between successive conversion steps in order to provide conversion of a major portion of said substrate into mannitol, and recovering mannitol and/or by-products of the conversion.

The preferred substrate is fructose. In the preferred bioconversion the solution also contains a co-substrate such as glucose.

The reconditioning of the solution is preferably performed in a sequential manner by adjusting one or more of the parameters of the conversion. The sequential reconditioning is preferably performed between distinct steps of the bioconversion.

In accordance with the present invention, the solution is preferably fed through a bed of immobilized microorganisms. The microorganism bed may be contained in a packed column or it may alternatively be located in an agitated reactor. In the preferred embodiment of the invention the solution is recirculated through a packed column and the solution is reconditioned as it leaves the bed, to be at its optimum for the next bioconversion sequence.

The feed solution is preferably sequentially reconditioned by adjustment of process parameters which change with time and conversion. This reconditioning according to the invention improves the conversion rate and/or the conversion yield of the process.

According to a preferred embodiment of the invention the substrate solution is sequentially reconditioned by intermittently adjusting the pH of the solution. The pH is preferably adjusted outside the actual microorganism bed by recirculating the solution through the bed and adjusting the pH between recirculations. Alternatively, the pH may be adjusted between beds in a system having several beds in series or in parallel. The beds are preferably contained in one or more columns. The solution may be fed at a relatively high flow rate through such columns.

In another embodiment of the invention, the solution is sequentially reconditioned by adjusting the concentration of mannitol producing substrate, such as fructose, or co-substrate, such as glucose, used by some microorganisms in the conversion. This reconditioning of the solution allows the process to proceed sequentially at optimum conditions.

It also allows a freedom in the selection of feed solution, since a solution having a low concentration of either substrate or co-substrate may be reconditioned to bring the solution up to optimum conditions.

It has also been found advantageous to sequentially adjust the temperature of the feed solution between recirculations and/or between beds or columns. The temperature of the solution should be adjusted to a value which is within the optimum temperature of the microorganism in question.

According to the present invention it has been found advantageous to proceed at a fairly high feed rate, which is enabled by the use of a packed column having the microorganisms immobilized on a substantially non-compressible carrier providing only a small resistance to flow. The feed rate may, however, also be adjusted e.g. between columns or, for instance by dividing the flow from one column into two.

A reconditioning, preferably in a sequential manner, of the nutrients in the feed solution is used according to the invention to provide, on one hand an optimum concentration of the basic nutrients necessary for the conversion, and on the other hand to intermittently refresh the immobilized microorganisms by subjecting them to conditions which provide sequential phases of increased growth with increased and supplemented nutrient feed.

In the process some conversion products are liable to cause a lowering of the conversion rate. The solution is preferably sequentially reconditioned by removal of such products by various means such as by filtration, crystallization, chromatography, ion exchange, reduction of pressure, neutralization by chemical additions, etc.

In many cases a combination of two or more of the above discussed reconditioning procedures will provide the desired optimum conditions for the conversion. It is also possible to direct part of the flow through a reconditioning step while the other part of the feed goes unconditioned. The flows may also be partitioned between different reconditioning steps in the phases between bioconversions.

According to the invention the aim is to perform said reconditioning in an amount sufficient to increase the conversion yield of mannitol compared to a non-conditioned state. Preferably, a sequential conditioning is performed so as to provide a conversion of at least 70%, preferably 80 to 90% or more of the feed fructose into mannitol.

According to a preferred embodiment of the invention the feed solution is recirculated through a bed of microorganisms to increase the mannitol yield and the volumetric productivity of the system. The feed solution may also be fed sequentially through several beds of microorganisms. The process is preferably performed as a continuous conversion in one or more columns packed with a carrier containing immobilized microorganisms.

The immobilized system according to the invention enables the use of high concentration of the microbe, feeding of simple solutions of substrate with very low concentrations of nutrients and steady production for a long period with the same immobilized microbial inoculum. All this results in a high mannitol yield from the substrate (generally fructose). Yields well above 50% and as high as 80–90% or more have been obtained. The system provides a very high volumetric productivity (above 10 g/lh and up to 30–40 g/lh) and steady production with one cell loading.

The crude conversion product contains basically just mannitol and acids such as lactic acid and acetic acid and there is no need for cell separation for the crude product. Thus, an exceptionally pure crude product is formed in the process. The substrate being converted to mannitol may be circulated back after the mannitol recovery step to sequentially increase the substrate concentration and thus to increase the conversion yield. The co-substrate may be similarly recirculated in the process. Likewise, part of the acids which are produced in the conversion may be circulated back from the recovery step to sequentially improve the aseptatic of the conversion.

The mannitol yield in recovery may also be increased after most of the mannitol has been separated from the mother liquor by recirculating the mother liquor after crystallization sequentially back to the process. Mannitol remaining in the mother liquor will thus add to the mannitol produced in the conversion.

The carrier which is useful in the performance of the present process should preferably be of a non-compressible material. It may be composed of an inert material such as porous glass beads, porous silicate beads, granulated activated charcoal, or solid acidic or basic ion exchange materials. Especially good results have been obtained on a commercial scale with a weakly basic anion exchange substance in the form of a substantially non-compressible porous-surface particulate solid material. A suitable cation exchanger comprises microfibers or microparticles of basic diethylaminoethyl (DEAE) modified cellulose adherently bound by agglomeration with polystyrene to form a granulate, such as acidified GDC carrier (e.g. Spezyme$^R$ GDC produced by Genencor International Oy).

Ion exchangers with a strongly acidic or a basic character have not been found suitable as carrier materials.

It is preferred that the microbe immobilized on or in the carrier metabolizes sugars solely through the pentose phosphate pathway, expresses mannitol dehydrogenase activity, produces no other main reduced products than mannitol eg. not ethanol and is a fermentative microbe. Several heterofermentative lactic acid bacteria are examples of such microbes. Among suitable microbes can be mentioned *Leuconostoc pseudomesenteroides, Aspergillus caidiaus, Zygosaccharomyces rouxii, Candida versatilis, Lactobacillus fermentum, Lactobacillus cellobiosus, Lactobacillus brevis, Lactobacillus buchneri, Leuconostoc mesenteroides* and *Leuconostoc oenos*. The preferred micro-organism is *Leuconostoc pseudomesenteroides* (ATCC 12291).

The invention is not, however, limited to these microbes and other microbes with a similar activity as well as microbes derived from such microbes, for instance by recombinant techniques, may be used in the process.

Metabolism of hexose sugars through the pentose phosphate pathway generates two reducing equivalents (AND(P)H) and one mole of pentose-5-phosphate per mole of hexose. From the one mole of pentose-5-phosphate one mole of lactic acid and one mole of acetic acid is produced in lactic acid bacteria. In this latter route there is no net consumption or production of reducing equivalents. Thus, the microbe needs a substrate to be reduced to consume the extra reducing equivalents. It is this substrate which is preferentially converted to mannitol. Most of the microbes used in the process are fermentative and thus do not need oxygen transfer.

Any assimilable hexose sugar or an oligo- or polysaccharide (eg. sucrose, lactose, maltose, starch, starch or cellulose hydrolysates, cellobiose, cellulose) hydrolyzable into such hexose sugars or complex sources containing these can be used as a co-substrate. The preferred substrate is fructose which is convertible to mannitol. In some cases mannose functions according to the invention as a substrate in an equivalent way to fructose and mannose may be included in the feed solution.

Suitable feed solutions thus include mixtures of fructose and glucose, inverted molasses and/or isomerized glucose. Glucose in a feed solution may be simultaneously or separately, preferably sequentially enzymatically isomerized in the process in a separate loop or in the same apparatus. The feed solution may comprise cane or beet molasses or fractions thereof. It may comprise thin or thick juices or even the run-offs from sugar production after first, second or third sugar crystallizations. In fact, any inverted sucrose containing material can be used as the feed material which is then reconditioned to provide a suitable solution for obtaining an optimum mannitol yield from the starting material.

The conversion process results in a crude product containing mannitol, acids such as lactic acid and acetic acid, as well as any unreacted components. If necessary or desirable, the crude product may be separated into one or several products. These products may, as described above, be recirculated to the conversion process to provide sequential reconditioning of the feed solution or they may be recovered and used for various separate purposes.

The recovery steps generally include one or more steps selected from the following non-limiting list of operations:
concentration of the crude product;
crystallization of mannitol;
chromatographic separation of the different products from the crude product;
concentration of those products;
crystallization of separated mannitol;
separation of products from the mannitol crystallization mother liquor; and
distillation of acetic acid and/or lactic acid.

The mother liquor after mannitol separation contains lactic acid and/or acetic acid and according to the invention this mother liquor may be used as an animal feed or a food or feed additive, e.g. as a preservative.

The above mentioned Soetaert et. al 1995 article teaches that the affinity of some of the mannitol dehydrogenases for fructose is rather low. This results in decreasing volumetric productivity near and below the $K_m$-value (about 7 g/l of fructose for *L. pseudomesenteroides*). To avoid this without loosing any fructose, the present invention preferably includes a chromatographic separation step for the crude product or for the mannitol crystallization mother liquor and recycling of the separated fructose back for sequential reconditioning in the conversion step. This method can be applied with any pair of enzyme and substrate having a low mutual affinity.

The optimum conversion conditions depend on the microbe being used. Especially the pH of the broth and the process temperature are important parameters and should be preferably sequentially adjusted into values suitable for the microbe. As acids are produced, the pH may be controlled by controlling the co-substrate consumption in such a way that the pH does not decrease too much. Alternatively, the feed solution may be buffered with a compatible buffer or the pH may be adjusted by sequential addition of a base such as sodium hydroxide. The base may be added to the feed solution in the sequence when said solution is circulating outside the bed, either between recirculations in one bed or column or between two consecutive beds or columns. The pH may also be adjusted by sequential removal of the acid byproducts from the solution.

The conversion generally produces carbon dioxide as a by-product. The carbon dioxide may be allowed to freely rise to the top of the bed or column or it may be retained in the solution by applying pressure on the column. In cases where $CO_2$ is released the column is preferably pressurized in order to prevent $CO_2$ gas from upsetting the flow pattern in the column. In cases where a pressure is applied to the column, also the pH of the feed solution may be sequentially adjusted by releasing the pressure between columns or between recirculations. This will reduce the amount of dissolved carbonic acid since carbon dioxide gas will be free to escape into the atmosphere.

It is essential for the present invention that the microbe being used is immobilized in and/or on a solid carrier. Soetaert et al. (1991) used polyurethane as a carrier with disappointing results. It has now been surprisingly found that it is possible to achieve a very good result with immobilized cells when operating in accordance with the present invention.

The bed of immobilized microorganism cells may be contained in any vessel with ports for feed and outflow. Circulation of the solution outside the bed should enable temperature control and preferably agitation and it should have ports for feed, outflow and addition of compounds such as pH controlling agents, nutrients, etc. Preferably the vessel is a column. Several columns may be used in series and/or in parallel.

The invention will now be described in detail with reference to a preferred embodiment of the invention. It should, however, be understood that this description is not intended in any way as limiting the invention to this specific embodiment.

The production organism is first grown on a liquid medium enabling efficient cell mass production. In this inoculum production phase enough nutrients are added to the medium to allow proper cell growth.

For the immobilization the inoculum is either circulated through a bed of carrier material in the production vessel or the carrier material is added to the inoculum and the cells are allowed to adhere to the material after which the material is transferred to the production vessel.

In the production step a feed solution containing the substrate and co-substrate is recirculated through the cell mass-carrier bed or fed through a series of beds.

The production vessel preferably comprises a column packed with the immobilized micro-organisms on a non-compressible carrier. The system may comprise one single bed with a recirculation system or it may comprise two or more columns in series or in parallel. The columns may, for instance, be placed on top of each other with feeding ports for pH-adjusting compounds, substrate and co-substrate, nutrients, etc. being placed between the columns.

When a substantially non-compressible carrier is used in the column, the column may be fairly high, for instance 1 meter or more, while still providing a flow rate at an acceptable level. The flow direction of the solution may be either down flow or up flow.

The volumetric flow is preferably maintained at such a rate that the production of acids in the bioconversion does not reach a level where it is prohibitive to mannitol production in the bed in question. To reach optimum mannitol concentrations the feeding is performed at a rate of 2–20 bed volumes per hour, preferably about 10–20 bed volumes per hour.

The pH of the solution is sequentially adjusted to recondition the feed solution to an optimum value for the specific microorganism being used. The pH may, for instance, be adjusted by an addition of a base such as NaOH, $NH_4(OH)$, KOH, etc. although other means of pH adjustment are described above. The pH should generally be reconditioned to a level between about 4 and 7, in most cases to between 4.5 and 6.5, preferably about 5.

The solution may be directed from the bioconversion stage in the bed to a intermediate vessel where pH adjustment is performed, or the pH adjustment may take place in a recirculation pipe or in a pipe leading from one column to another.

The temperature of the solution may be sequentially adjusted so as to provide close to optimum conditions for the conversion. Adjusting the temperature of the solution to a value of about 20 to 35° C., preferably 25 to 30° C. has been found to be advantageous.

Typical substrate (fructose) concentrations are 7–200 g/l, preferably 15–160 g/l, most preferably about 50–150 g/l, with corresponding co-substrate (glucose) concentrations of 4–100 g/l, preferably 8–80 g/l, most preferably about 25–75 g/l. The conversion rate is significantly lowered if the fructose concentration decreases under the $K_m$ value of the microorganism in question. The solution should therefore be reconditioned to have a fructose level clearly above the $K_m$ value by adding fructose sequentially between conversion phases.

It is advantageous to utilize the cell mass in a resting state during the actual bioconversion phase, wherefore very low nutrient concentrations are required in the normal feed solution. Typically yeast extract and/or tryptone in concentrations of 0.1–4 g/l is sequentially fed to the solution outside the bed. This low nutrient level is possible because the cell mass is retained by the carrier in the vessel and mannitol conversion phase needs no cell growth. The conversion rate is dependent on the total amount of active cell mass in the bed. The sequential low-level addition of nutrients will intermittently refresh the microbial activity of the cells.

As conversion proceeds, the effectivity of the bed will be gradually lowered by a lack of viable cells in the bed. Thus, a refreshing of the cell mass in the bed should be performed by preferably sequentially feeding an increased amount of nutrients to the solution for allowing the microorganisms to grow and to increase the microbial density on the carrier. The nutrients generally comprise contains yeast extract, tryptone, $Na_2HPO_4$, magnesium sulphate and/or manganese sulphate.

Preferentially alternating production and refreshing cycles are performed with the same cell mass loading. When the volumetric productivity has decreased below a threshold value, a refreshing phase is started by the addition of nutrients into the feed solution. The nutrient adding sequence is maintained until a higher threshold value for the volumetric productivity is achieved. Volumetric productivity can be estimated e.g. from the consumption rate of pH controlling agent.

A reconditioning of the solution may also be performed by removing solid or liquid components from said solution. The solution may be subjected to filtration, precipitation, elution, membrane filtration, electrodialysis, fractional distillation, etc. to remove selected components thereof.

As the carrier material is of a durable and non-compressible structure it may be re-used even after the cell mass has reached a stage where refreshing and growth no longer provides a satisfactory conversion rate. Especially the above mentioned DEAE modified cellulose/polystyrene carrier, GDC, is capable of being regenerated. This is performed by removal of the micro-organism cells, washing and reloading the carrier with fresh viable micro-organism cells.

After a desired bioconversion phase, the solution is taken to the recovery phase. This may be started before all substrate being converted to mannitol is consumed. This is advantageous in cases where the productivity and/or yield diminishes with low substrate concentration. For example, this is the case when *L. pseudomesenteroides* is used for converting fructose. To avoid loosing this unconsumed substrate, the fructose is separated in the recovery phase and circulated back to the conversion step for reconditioning the feed solution.

Contamination with foreign organisms is a frequent problem in fermentation. A mixture of lactic acid and acetic acid is inhibitory to most microbes. This can be utilized in the present invention by separating the acids in the recovery step and circulating part of them back to the conversion step to provide a sequential reconditioning of the feed solution.

In the recovery step mannitol can be directly crystallized with known techniques from the crude product after the conversion step. If complex materials are being used, color removal may be necessary before crystallization. Mannitol may also be crystallized from the solution between the bioconversion sequences to recondition the feed solution for the subsequent conversion stage.

Other sugars, if present, may be separated from the other components e.g. by chromatography and circulated back to the conversion step.

The acids produced in the conversion may be separated from the crystallization mother liquor by chromatography e.g. using a cation exchange resin in Na-form or by using ion-exchange techniques. Alternatively, the mother liquor may be used as such as an antimicrobial agent or used as described above for sequential reconditioning.

In the following the invention will be illustrated by some non-limiting examples.

EXAMPLE 1

Immobilisation of the Microorganism in a Column Reactor

*L. pseudomesenteroides* (ATCC 12291) was inoculated from a storage cultivation onto a growth medium having the following composition: 100 g/l fructose, 50 g/l glucose, 2 g/l yeast extract, 2 g/l tryptone, 2 g/l $K_2HPO_4$, 0.01 g/l $MgSO_4$, 0.01 g/l $MnSO_4$.

The inoculum was allowed to grow over night and the cell mass was then transferred to a desinfected (70% ethanol) carrier by recirculating the growth medium through a column packed with carrier for 2 hours. The carrier was a weakly basic anion exchange (Spezyme$^R$ GDC carrier made of microfibers of DEAE modified cellulose bound together with polystyrene, produced by Genencor International Oy).

EXAMPLE 2

Immobilisation of the Microorganism in an Agitated Reactor

The same microorganism cell mass was used as in Example 1. The microbial cell mass was added to a reactor containing a disinfected carrier and the mixture was agitated for two hours until the microorganisms had adhered onto the carrier. Thereafter the reactor was ready for bioconversion.

EXAMPLE 3

Sequential Reconditioning by Adjusting pH and Temperature

The column provided in accordance with Example 1 (bed volume 1 liter) as used in the test. A sterilized feed solution (volume 10 liters) was recirculated through the column. The feed solution had the following composition: 150 g/l fructose, 50 g/l glucose, 1 g/l yeast extract, 1 g/l tryptone, 0.01 g/l $MgSO_4$, 0.01 g/l $MnSO_4$. The recirculation direction was from top to bottom of the column.

The temperature and pH of the feed solution was sequentially adjusted between bio-conversion phases in a recirculation vessel. The temperature was adjusted to about 25° C. and the pH was adjusted to 5.0 by sequentially adding NaOH (16%).

The feed rate through the column was maintained at a constant value to provide a retention in the column of about 6 min.

After a total process time of 43 hours the composition of the feed solution was analyzed and it was found to contain: 127 g/l mannitol, 32 g/l D-lactate, 22 g/l acetate, 2 g/l fructose and 0.3 g/l glucose. The average volumetric mannitol production rate per column volume was calculated to be 30 g/lh. The mannitol yield from fructose was about 85%

The solution was evaporated to a 60% dry substance content and the mannitol was crystallized from the solution by gradually cooling the solution to 32° C.

EXAMPLE 4

Sequential Reconditioning by Adjusting Nutrient Feed

The recirculated batch process of Example 3 was repeated after the first converted solution had been discharged from the recirculation vessel to mannitol recovery. The recirculation vessel was refilled with a new feed solution having the same composition as the one used in Example 3.

The converted solution after the second conversion had a composition which did not significantly differ from the one obtained in the first run.

New batches of feed solution were converted in the same manner until the conversion rate, measured by the rate at which pH adjusting NaOH was consumed, decreased below a threshold value.

When the threshold value was set at 10 g/lh, the batches could be repeated for 3 to 4 runs. Thereafter the microorganisms in the column were refreshed by circulating a nutrient-rich solution containing 100 g/l fructose, 50 g/l glucose, 2 g/l yeast extract, 2 gal tryptone, 2 g/l $K_2HPO_4$, 0.01 g/l $MgSO_4$ and 0.01 g/l $MnSO_4$ through the column, until the pH adjusting NaOH consumption rate increased to a desired level (for about 3–5 hours). Thereafter the column was again used for conversion according to Example 3.

EXAMPLE 5

Production of Mannitol From Different raw Materials

By utilizing the over-all procedure described in Example 3 mannitol was produced in a recirculated packed column reactor from various raw materials and using various carrier materials. The microorganism used was *L. pseudomesenteroides* (ATCC 12291). All of the carriers and raw materials produced mannitol under the process conditions.

The raw materials and carriers of the tests are presented below:

TABLE 1

| Raw material | Carrier |
| --- | --- |
| Pure fructose-glucose mixture (3:1) | GDC (DEAE) |
| as above | GDC (COO$^-$) |
| as above | glass beads |
| as above | Norton catalyst |
| Beet molasses fully inverted with invertase (sugar 50 g/l) | GDC (DEAE) |
| as above | glass beads |
| Glucose (50 g/l) isomerized to glucose/fructose (40:60) | GDC (COO$^-$) |
| as above | Norton catalyst |

The carrier materials used were:
GDC (DEAE) = Spezyme ® GDC a weakly basic anion exchanger produced by Genencor International Oy
GDC (COO$^-$) = a weakly acid cation exchanger an experimental product by Cultor Ltd
Norton catalyst = a catalyst carrier, SA 5203 ⅛" from Norton Chemical Products Corporation

EXAMPLE 6

Production of Mannitol With Different Carrier Materials

*L. pseudomesenteroides* was immobilized on various carrier materials by cultivation in the presence of the carrier materials in MRS broth containing 40 g/l fructose. The concentration of the carrier material was 40 g/l and the cultivation in a shake flask was continued up to 20 hours at shacking rate 100 rpm at 25° C. The carrier material with the cells attached on it was separated from the broth and loaded into a column.

Mannitol production was demonstrated by circulating a solution containing 10 g/l glucose, 30 g/l fructose, 2 g/l $Na_2HPO_4$, 2 g/l $NaH_2$-citrate and 3 g/l acetic acid through the column. The pH was controlled to pH 5.2 with NaOH. Mannitol was analyzed by HPLC from samples taken after 3 hours circulation.

The carrier materials were Spezyme$^R$ GDC, Norton catalyst, glass beads (Schott beads, SIRAN carrier, SIKUG 023/02/B, Schott Engineering), activated carbon (granulated activated carbon, Chemviron CPG), Amberlite IRA 93 (a weakly basic anion exchanger, Rohm & Haas), and GDC (COO$^-$).

EXAMPLE 7

Production of Mannitol With Different Immobilized Micro-organisms

*L. brevis* (VTT-E-91458) was immobilized on Norton catalyst as described for the *L. pseudomesenteroides* in Example 6.

*Aspergillus candidus* (NRRL 305) was immobilized by cultivating it for 68 h in shake flasks at a shaking rate of 250 rpm at 28° C. in Czapek broth containing 30 g/l sucrose and 5 g/l yeast extract and 40 g/l Spezyme$^R$ GDC. The carrier material with the organism attached on it was recovered from the broth by filtration.

In a similar way *Zygosaccharomyces rouxii* (ATCC 12572) was immobilized on Spezyme$^R$ GDC but using YM broth, *Candida versatilis* (ATCC 20221) and (ATCC 20223) were immobilized on glass beads using ATCC broth 466.

Short-term mannitol production at acceptable levels was demonstrated with the immobilized materials with the following production media:

| | |
|---|---|
| *L. brevis:* | 30 g/l fructose, 10 g/l glucose, 2 g/l Na$_2$HPO; sequential adjustment of pH to 5.2 |
| *A. candidus:* | 100 g/l glucose, 1 g/l yeast extract, 0.5 g/l NaNO$_3$; sequential adjustment of pH to 7.3 |
| *Z. rouxii:* | 200 g/l glucose, 1 g/l yeast extract, 0.5 g/l urea; no pH adjustment |
| *C. versatilis:* | 200 g/l glucose, 1 g/l yeast extract, 2 g/l K$_2$HPO$_4$; sequential adjustment of pH to 5.5. |

EXAMPLE 8

Crystallization of Mannitol

A filtered mannitol solution obtained according to the process of the present invention was subjected to crystallization. The dilute mannitol solution containing about 63% mannitol on DS was evaporated to a concentration of about 48% by weight. The resulting solution was cooled to a temperature of about 45° C. and seeded by spontaneous crystallization. The crystallized mannitol mass was cooled in about 12 hours to a temperature of about 32° C. The crystals were separated from the mother liquor by centrifugation and dried. In the centrifugation about 50% washing water on DS was used and crystals were dried in an oven at 40° C.

The mannitol yield was about 25% on DS and about 40% on mannitol after the centrifugation.

EXAMPLE 9

Separation of Mannitol From Mother Liquor

Mannitol was crystallized from a conversion solution according to Example 8 and the crystals were separated from the mother liquor by centrifugation. In order to purify the mannitol still left in the mother liquor, a chromatographic separation of the solution was done. The separation was performed in a chromatographic separation column as a batch process.

A separation column was filled with a strongly acidic cation exchange resin (manufactured by Finex Oy, Finland) and submerged in water. The degree of cross linking the resin was 6.0% DVB and the average particle size about 0.35 mm. The resin had been regenerated to Na$^+$-form with NaCl-solution.

Before the separation, the feed solution was filtered and the dry substance (DS) content was adjusted to 30 g/100 g. The pH of the feed solution was adjusted to pH 5.5 with sodium hydroxide. The process temperature was adjusted to 80° C. and the linear flow rate of the eluent water in the column to about 0.5 m/h.

Conductivity, pH, refractive dry substance (RDS) and the composition of residual and product fractions (by HPLC) were analyzed. The compositions of the fractions and feed solution are presented in Table 2. The fractions were analyzed by HPLC.

TABLE 2

Composition of fractions, feed solution and mannitol yield

| | Feed solution | Residual fraction | Product fraction |
|---|---|---|---|
| RDS, g/100 g | 30 | 6.5 | 7 |
| Mannitol, % on DS | 48.5 | 5 | 90 |
| Glucose, % on DS | 0.4 | — | 0.8 |
| Fructose, % on DS | 1.8 | — | 3.5 |
| Acetic acid, % on DS | 19 | 56.5 | 2.8 |
| Lactic acid, % on DS | 29 | 37 | 2 |
| Mannitol yield, % | | 5 | 95 |

What is claimed is:

1. A process for the production of mannitol comprising introducing a feed solution containing fructose into a zone comprising solid non-compressible carrier particles that contain viable mannitol-forming micro-organism cells immobilized in or on said particles, wherein said zone is under continuous fermentation conditions;

biochemically converting said feed solution containing fructose in said zone into a solution containing mannitol;

reconditioning said solution containing said mannitol by readjusting process parameters which have changed during said converting step, wherein said reconditioning is monitored to provide a volumetric production rate of mannitol per column volume between about 30 and 40 g/l in said conversion;

recirculating the reconditioned solution into said zone or into another zone; repeating said converting, reconditioning, and recirculating steps to obtain a conversion of more than 70% of said fructose into mannitol; and recovering mannitol and optionally by-products of the conversion.

2. The process according to claim 1, wherein said reconditioning of said solution comprises sequential adjustment of pH, temperature, feed rate, substrate content, co-substrate content, nutrient feed or pressure, removal of conversion products or other solid or liquid components, or combination of any of the foregoing.

3. The process according to claims 1 or 2, wherein said reconditioning step is performed on a part of said solution or different parts of said solution are subjected to different reconditioning steps.

4. The process according to claim 1, wherein said carrier particles comprise a porous material.

5. The process according to claim 1, wherein said process is a continuous conversion process performed successively in one or more columns packed with said carrier.

6. The process according to claim 4 or 5, wherein said solution is recirculated through one or more of said columns.

7. The process according to claim 4 or 5, wherein said solution is fed successively through a series of said columns.

8. The process according to claim 4, wherein said carrier comprises an inert material selected from the group consisting of porous glass beads, porous silicate beads and active charcoal.

9. The process according to claim 4, wherein said carrier comprises a weakly basic anion exchange substance in the form of a substantially non-compressible porous particulate solid material.

10. The process according to claim 1, wherein said micro-organisms are selected from the group consisting of *Leuconostoc pseudomesenteroides, Aspergillus candidus, Zygosaccharomyces rouxii, Candida versatilis, Lactobacillus fermentum, Lactobacillus cellobiosus, Lactobacillus brevis, Lactobacillus buchneri, Leuconostoc mesenteroides* and *Leuconostoc oenos.*

11. The process according to claim 9, wherein said micro-organism is *Leuconostoc pseudomesenteroides* (ATCC 12291).

12. The process according to claim 1, wherein said reconditioning step comprises adjusting the pH of said solution to a value above about 4.

13. The process according to claim 1, wherein said reconditioning step comprises adjusting the pH of said solution to a value between about pH 4.5 and 6.5.

14. The process according to claim 1, wherein said reconditioning step comprises adjusting the pH to a value of about pH 5.

15. The process according to any one of claims 12, 13 and 14, wherein the pH of said solution is adjusted by adding a base selected from the group consisting of an alkali hydroxide and ammonium hydroxide or by adding a buffering substance.

16. The process according to any one of claims 12, 13 and 14, wherein the pH of said solution is adjusted by removing acid formed during the conversion.

17. The process according to claim 16, wherein carbonic acid formed by dissolution of carbon dioxide produced during the conversion is removed by reducing the pressure of said solution.

18. The process according to claim 1, wherein said reconditioning step comprises adjusting the temperature of said solution to about 20 to 35° C.

19. The process according to claim 1, wherein said reconditioning step comprises adjusting the volumetric flow rate of said solution to a value of about 2 to 20 bed volumes per hour.

20. The process according to claim 1, wherein said reconditioning step comprises adjusting the substrate fructose content of said solution to about 7 to 200 g/l.

21. The process according to claim 1, wherein said reconditioning step comprises adding a co-substrate to said solution to about 4 to 100 g/l.

22. The process according to claim 1, wherein said reconditioning step comprises adding nutrients to said solution.

23. The process according to claim 22, wherein said nutrients are selected from the group consisting of yeast extract, tryptone, $Na_2HPO_4$, magnesium sulphate, manganese sulphate and mixtures thereof.

24. The process according to claim 1, wherein said reconditioning step comprises recovering mannitol between successive conversion steps.

25. The process according to claim 24, wherein said reconditioning step comprises returning any substrate remaining in the mother liquor after final mannitol recovery to said solution.

26. The process according to claim 24, wherein said reconditioning step comprises recovery of acids from said solution by chromatography or ion exchange.

27. The process according to claim 25, wherein said reconditioning step comprises returning at least a part of said mother liquor to said solution.

28. The process according to claim 1, wherein said reconditioning step comprises removing solid or liquid components contained in said solution by one or more processes selected from the group consisting of filtration, precipitation, elution, membrane filtration, electrodialysis, and fractional distillation.

29. The process according to claim 6, wherein said solution is recirculated through said column until the volumetric production rate of mannitol per column volume in said column has decreased to a predetermined threshold value.

30. The process according to claim 1, wherein said solution contains as a co-substrate an assimilable hexose sugar, selected from the group consisting of glucose, an oligo- or poly-saccharide hydrolyzable to a hexose sugar, and a mixture thereof.

31. The process according to claim 30, wherein said solution contains a mixture of fructose and glucose.

32. The process according to claim 31, wherein said solution comprises isomerized glucose, inverted molasses, beet or cane molasses, thin or thick juices or fractions thereof.

33. The process according to claim 31, wherein the glucose in said solution is simultaneously enzymatically isomerized in the process.

34. The process according to claim 1, wherein said solution contains glucose or mannose as said substrate convertible into mannitol.

35. The process according to claim 1, wherein the carrier is regenerated by removal of the micro-organism cells, washing and reloading with fresh viable micro-organism cells.

36. The process according to claim 1, wherein said mannitol is recovered from the final converted solution by crystallization.

37. The process according to claim 36, wherein lactic acid or acetic acid contained in the mother liquor after mannitol separation are recovered by chromatography or ion exchange.

38. The process according to claim 1, wherein the conversion is performed until about 80% to about 90% or more of the fructose in said solution has been converted to mannitol.

39. The process according to claim 18, wherein said reconditioning step comprises adjusting the temperature of said solution to about 25 to 30° C.

40. The process according to claim 19, wherein said reconditioning step comprises adjusting the volumetric flow rate of said solution to a value of about 10 to about 20 bed volumes per hour.

41. The process according to claim 20, wherein said reconditioning step comprises adjusting the substrate fructose content of said solution to about 15 to 160 g/l.

42. The process according to claim 41, wherein said reconditioning step comprises adjusting the substrate fructose content of said solution to about 50 to 150 g/l.

43. The process according to claim 21, wherein said reconditioning step comprises adding a co-substrate to said solution to about 8 to 80 g/l.

44. The process according to claim 43, wherein said reconditioning step comprises adding a co-substrate to said solution to about 25 to 75 g/l.

45. The process according to claim 26, wherein said reconditioning step comprises returning at least a part of said recovered acid to said solution.

46. The process according to claim 33, wherein glucose in said solution is separately enzymatically isomerized in the process.

47. The process according to claim 31, wherein glucose in said solution is sequentially enzymatically isomerized.

48. The process according to claim 9, wherein said carrier comprises a weakly basic anion exchanger containing diethylaminoethyl (DEAE) modified cellulose adherently bound by agglomeration with polystyrene.

* * * * *